United States Patent [19]
Houben et al.

[11] Patent Number: 5,919,216
[45] Date of Patent: Jul. 6, 1999

[54] SYSTEM AND METHOD FOR ENHANCEMENT OF GLUCOSE PRODUCTION BY STIMULATION OF PANCREATIC BETA CELLS

[75] Inventors: Richard P. M. Houben, CT Berg & Terblijt; Alexis C. M. Renirie, AC Berg en Dal, both of Netherlands

[73] Assignee: Medtronic, Inc., Minneapolis, Minn.

[21] Appl. No.: 08/876,610

[22] Filed: Jun. 16, 1997

[51] Int. Cl.$^6$ .................................................. A61N 1/18
[52] U.S. Cl. ............................................................ 607/72
[58] Field of Search .............................. 607/72, 73, 74.3; 604/31, 50

[56] References Cited

U.S. PATENT DOCUMENTS

| | | |
|---|---|---|
| 4,003,379 | 1/1977 | Ellinwood, Jr. . |
| 4,403,984 | 9/1983 | Ash et al. .................................. 604/50 |
| 4,431,004 | 2/1984 | Bessman et al. . |
| 4,704,029 | 11/1987 | Van Heuvelen ........................... 356/39 |
| 5,101,814 | 4/1992 | Palti . |
| 5,113,859 | 5/1992 | Funke . |
| 5,165,407 | 11/1992 | Wilson et al. . |
| 5,190,041 | 3/1993 | Palti . |
| 5,231,988 | 8/1993 | Wernicke et al. . |
| 5,362,307 | 11/1994 | Guy et al. .................................. 604/20 |

OTHER PUBLICATIONS

"Kinetics of Intraperitoneally Infused Insulin in Rats—Functional Implications for the Bioartificial Pancreas"—Paul De Vos et al. (Diabetes, vol. 45, Aug. 1996).

"Pancreatic B Cells Are Bursting, But How?"—Daniel L. Cook et al. (TINS, vol. 14, No. 9, 1991).

*Primary Examiner*—Scott M. Getzow
*Attorney, Agent, or Firm*—Michael J. Jaro; Harold Patton

[57] ABSTRACT

There is provided a system for automatically responding to insulin demand without any need for external monitoring or injecting of insulin into the diabetic patient. The system provides for sensing glucose levels internally, and responding by stimulating either the pancreas or a transplant of pancreatic islets in order to enhance insulin production. The enhancing stimulation is delivered at a rate greater than the burst rate, or is otherwise controlled so that the depolarization burst constitutes a greater portion of each islet electrical cycle, thereby resulting in increased insulin production. The system also provides for continuous glucose monitoring, and reacts to sensed hypoglycemia by delivering stimulus pulses timed to reduce the burst durations, and thus to inhibit insulin production. In another embodiment, the system responds to a good intake signal, either externally or internally generated, by going through a time response algorithm to provide a stimulation-enhanced insulin response which simulates the natural response. In yet another embodiment, the functionality of an islet transplant is continually monitored, and performance data is logged and down loaded on command to an external programmer. The stimulation of patient pancreatic cells may be combined with administration of a hypoglycemic agent.

56 Claims, 13 Drawing Sheets

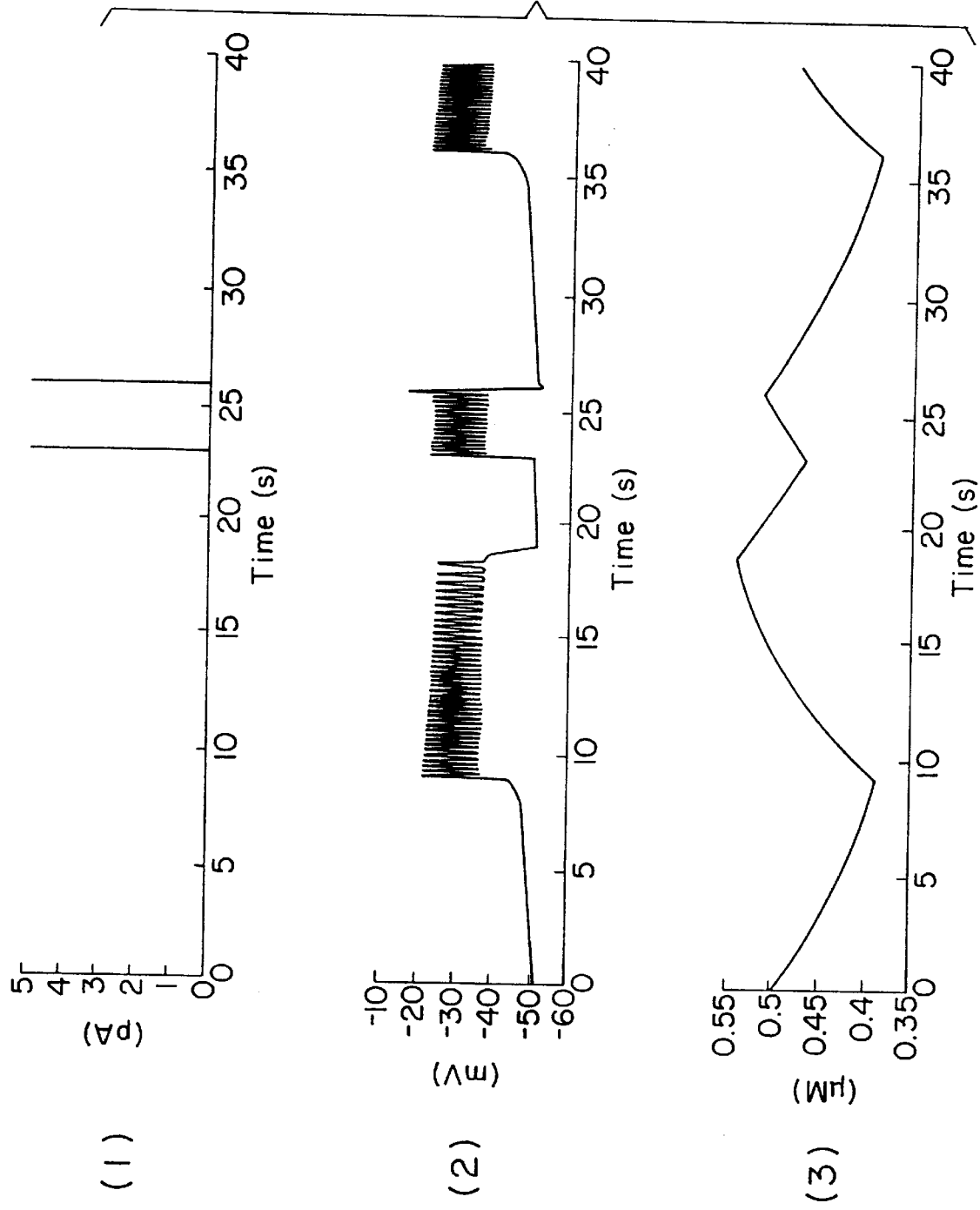

SYSTEM AND METHOD FOR ENHANCEMENT OF GLUCOSE PRODUCTION BY STIMULATION OF PANCREATIC BETA CELLS

FIELD OF THE INVENTION

This invention relates to systems for treatment of diabetes mellitus and, in particular, systems and methods for stimulating transplants of pancreatic islets and/or the patient's pancreas so as to enhance glucose production.

BACKGROUND OF THE INVENTION

It is known, from statistics published in 1995, that the number of diabetes patients in the United States is about 7.8 million, or about 3.4% of the total U.S. population. This number has been steadily rising over the past 25 years. Approximately 10%, or about 0.8 million such patients are insulin dependent (IDDM) patients. Further, of the remaining approximately 7 million non-insulin dependent diabetes mellitus (NIDDM) patients, about 30% use insulin. The percentage of NIDDM patients receiving insulin treatment increases with the duration of NIDDM from 25% (0–4 years) to 60% (greater than 20 years). From these statistics, it is seen that there is a substantial and an increasing need for a convenient and reliable system for eliminating the need of insulin injections for IDDM patients in particular, as well as for many NIDDM patients who receive insulin treatments.

One approach to providing insulin so as to eliminate the need of insulin injections is the transplant of encapsulated islets (Xeno, allo and auto type) of Langerhans. Research in the field of encapsulating islets by means of immunoisolative membranes has been extensively addressed, but a number of obstacles to this approach remain to be overcome. The technical aspects of the encapsulation process, i.e., how to improve the mechanical and chemical aspects of the capsules, are being addressed. See, for example, U.S. Pat. No. 5,190,041, which discloses capsules containing glucose-sensitive cells such as islets of pancreatic beta cells. Work is also progressing with respect to increasing survival times of such encapsulated islets, e.g., from months to years, or even a lifetime. However, other functional aspects of such capsules provide greater difficulties. Specifically, adequate restoration of normoglycaemia, as well as normal response to physiologic glucose stimulus, requires optimal glucose and insulin kinetics between the transplant and the blood stream. The most commonly used transplant sites, intra-portal as well as the intra-peritoneal cavity, present specific kinetic problems. Alternative transplantation sites in close contact to the blood stream do not permit sufficiently high volume transplants. Although the lack of physical volume might be offset by improving the effectiveness of the islets, functional limitations remain substantial. Further, the limited ability to respond to elevated blood glucose values with an appropriate insulin response remains a problem.

The overall object of this invention is to provide an improved insulin response to a diabetic patient, without need for insulin injection. The problem points to modifying or somehow changing the normal behavior of the transplant, or the patient's pancreas, so as to increase insulin production. Further, with respect to transplanted encapsulated islets, there is a need for improved kinetics since the transplant does not receive normal glucose signals. Although normoglycaemia can be reached with a transplant, an optimum physiological response to a glucose stimulus requires taking into account the blood glucose and insulin kinetics. For an intra-peritoneally transplanted islet graft, glucose kinetics is limited by diffusion from the blood stream towards the peritoneal fluid and towards the capsule, entrance to the membrane, spreading of the glucose over the islets by passive diffusion and the accomplishment of an insulin response by the islets. Insulin kinetics are determined by diffusion of insulin through the capsule membrane and the peritoneal fluid. Finally, the systemic blood vessel wall is reached and the insulin diffuses into the portal circulation, first passing the liver, and then entering the systemic circulation.

The primary mechanisms involved in the synthesis and exocytosis of insulin are largely known. At glucose concentrations below three mM, the beta cell is electrically silent with a resting membrane potential of about −70 mV. The resting potential is principally determined by the activity, (i.e., open-close probability state) of the ATP dependent outward potassium channels, i.e., the K-ATP channel. As a consequence of raising external glucose, as with food in-take, the ATP:ADP ratio increases, which leads to the closure of K-ATP channels, limiting outward flow of potassium, opening of voltage gated inward calcium (VGIC) channels and subsequent depolarization of the membrane. This mechanism implements the physiological glucose sensor. If the glucose level is greater than 4 mM, depolarization is sufficient to reach the threshold potential of about −40 mV, at which electrical activity is initiated. A subsequent rise in free cytosolic calcium triggers insulin secretion and activates calcium gated outward potassium channels, enhancing potassium efflux, which in turn inactivates VDDC, leading to cell repolarization. The electrical activity typically shows slow oscillations of depolarization (slow waves) with super imposed higher frequency burst activity during such depolarized burst episodes. During burst activity, spikes are seen with peak amplitudes of about 20 mV on a plateau of −30 mV. The firing frequency of a burst decreases gradually until repolarization.

It is known that beta cells can be activated by electrical field stimulation; further, beta cells in the pancreas can be activated by stimulation of the vagal nerve. As discussed further below, the burst length of a stimulated depolarization is substantially of equal length as a spontaneous depolarization. To achieve capture, i.e., to trigger the depolarization burst, the electrical stimulation pulse needs to exceed the membrane potential threshold, e.g., about −40 mV. From literature studies, it is known that a transmembrane current of 3 micro amperes is subthreshold, while a 4 microampere pulse achieves islet activation. Likewise, the burst activity can be terminated by a stimulus pulse which even further depolarizes the membrane, causing subsequent closure of voltage gated inward calcium channels, leading to premature repolarization. What has heretofore remained unknown is a capability of increasing insulin release from pancreatic beta cells (oxocytosis) by stimulation of the beta cells directly, or by nerve stimulation.

SUMMARY OF THE INVENTION

In view of the above, it is a specific object of this invention to provide apparatus and methods for elevating the secretion of insulin, either from an islet transplant or from the patient's pancreas, by sensing islet activity and then stimulating the pancreatic beta cells at a somewhat higher rate than the spontaneous slow wave rate. Further, it is an object to incorporate information concerning glucose and insulin diffusion kinetics, so as to obtain an improved response to glucose. With respect to transplanted islet grafts, autonomous nervous influences are lost, such that preproduction or anticipated production of insulin as a direct result of food intake, is not available. However, such pre-production can be restored upon receipt of a signal indicating food intake, by structuring an appropriate time response for increasing insulin production. At the same time, care must be taken not to induce hypoglycemia by excessive insulin production. This can be avoided by programming a break in insulin production after a predetermined interval in order to check for glucose level, after which insulin production can adjusted accordingly, i.e., inhibited.

In view of the above objects, there is provided a system and method for enhancing insulin production by apparatus implanted in a patient who needs insulin treatment. Enhanced production can be accomplished either by increasing insulin yield, or by achieving substantially equal yield with a reduced volume transplant. Enhancing stimulation is effected upon a transplant of pancreatic islets, or directly upon the patient's pancreas, or both. With respect to the pancreas, the stimulation might be either direct, or by the vagal nerve. The system monitors the spontaneous timing of the pancreatic beta cells, and schedules delivery of stimulus pulses at an increased rate relative to the spontaneous rate, so as to evoke depolarization bursts at a greater rate, yielding a higher duty cycle of insulin-producing depolarization bursts relative to the entire slow cycle (which also includes a repolarization period). In the course of stimulation, the system monitors glucose level and adapts the insulin-enhancing activity as a function of monitored glucose level. When a patient initiates eating, a stimulation intensity profile is introduced which simulates the insulin and glucose kinetics, to provide a more natural and optimal insulin response. The stimulation may be combined with the administration of a hypoglycemic agent.

In another embodiment of this invention, stimulation of the pancreas or islet transplant is performed to react to sensed hypoglycemia, with stimulus pulses being delivered before the end of respective depolarization bursts so as to shorten the insulin-producing bursts and reduce insulin production. Thus, this system is provided with the capacity of continuously monitoring both glucose level and insulin production, and responding by corrective action to either stimulate cells to increase insulin production or to decrease insulin production.

In the system of this invention, the glucose level is obtainable by any one of several different means. Thus, the glucose level can be obtained by stimulating the pancreatic cells so as to synchronize the depolarization bursts and create the conditions for optimal sensing of burst parameters, whereby insulin demand (and thus glucose level) is determined. See U.S. patent Ser. No. 08/876,738, filed concurrently with this application, "System for Pancreatic Stimulation and Glucose Measurement", file P-4971. Alternately, glucose can be sensed by monitoring EKG signals and deriving a measure of glucose therefrom. In yet another alternate embodiment, glucose can be sensed from a second transplant located close to the blood stream, the second transplant being utilized specifically for sensing purposes. In still another embodiment, the glucose signals may be received from an external programmer.

The system and method of this invention provides for an improved insulin response by timing insulin delivery relative to initiation of a glucose increase due to food intake. Glucose load can be determined automatically as by sensing filling of the stomach. Alternately, the patient provides an externally generated signal indicative of the start of eating, and the implanted device calculates stimulation patterns, i.e., timing and intensity, corresponding to insulin and glucose kinetics. Under control of an algorithm for calculating the optimum stimulation pattern, the insulin enhancement is undertaken, either to increase insulin release by stimulation of the pancreas or a transplant, or to directly control an insulin pump. The glucose level is periodically monitored, and the insulin response is adjusted accordingly.

In yet another embodiment of this invention, transplant functionality is tested. Following administration of a glucose load, the islet activity is sensed, both with and without stimulation. The correspondence of islet activity relating to glucose load is analyzed, and the data is transmitted to an external programmer for diagnostic purposes, or is used to adjust the parameters of the insulin-enhancing stimulation. The obtained data can be used for recalibration or adjustment of stimulation parameters, or may be logged for subsequent retrieval by the physician, e.g., as an indicator of the quality of metabolic control such as $HbA_{1c}$. Logged information can include the number and length of hypo and hyper glycemic episodes, postprandial glucose profiles, nocturnal hourly averages, etc.

In another embodiment of the invention, multiple electrodes are positioned in the pancreas, and stimulation is periodically switched to a different pair of electrodes, to mitigate the "overworked beta cell" effect.

BRIEF DESCRIPTION OF THE DRAWINGS

FIG. 8A is a series of timing diagrams illustrating stimulation which is programmed to react to hypoglycemia by inhibiting insulin production.

DESCRIPTION OF THE PREFERRED EMBODIMENTS

Figure 1:
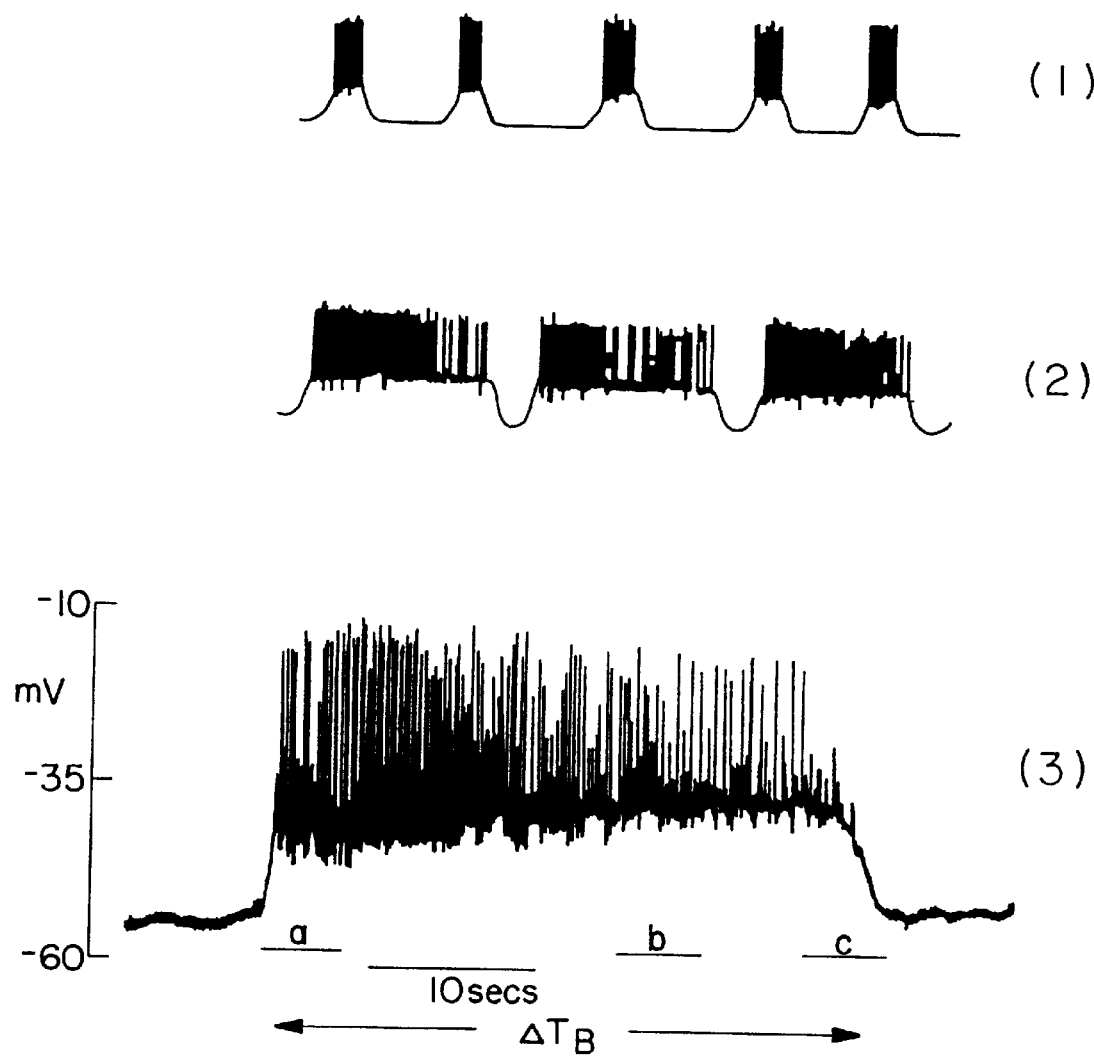
FIG. 1 is a drawing showing the electrical activity of pancreatic islets of beta cells, illustrating the slow wave cycles comprising depolarization and repolarization portions.

Referring to FIG. 1, there are shown three timing diagrams illustrating burst behavior of pancreatic beta cells. In the upper diagram, designated (1), the duty cycle, defined as the fraction of the burst duration compared to the overall depolarization-repolarization cycle, is relatively small. This represents a condition where glucose levels are low to moderate, and there is relatively little demand for insulin. Diagram (2) illustrates a situation of greater insulin demand characterized by a much higher duty cycle, with corresponding greater burst activity and concurrent insulin production. Note that in an extreme situation, the burst activity can be virtually continuous, i.e., approaching a duty cycle of 1. The curve illustrated at (3) is a blown up depiction of the burst, or depolarization plateau of the low frequency beta cell cycle. It is seen that the onset of depolarization is rather sharp, followed by relatively high frequency spiking. Toward the end of the burst period, the spike frequency is seen to diminish, and then the electrical activity simply tails off. However, the end of the burst period as shown in this representation is sharp enough to be able to define with substantial accuracy the end of burst time. It is noted that mean spike frequency carries information reflective of glucose level, but the duration of the burst, indicated as $\Delta T_B$, is the primary indication of insulin demand, and thus blood glucose level. As used in the claims of this invention, the terms "insulin demand" and "glucose level" and "blood glucose level" are used interchangeably. Either $\Delta T_B$ or $\Delta T_B$ as a fraction of the low frequency depolarization-polarization cycle, may be used to determine the glucose level. As used herein, the phrase burst parameters refers to burst duration, duty cycle, spike frequency, or any other parameter of the beta cell signal from which a measure of glucose or insulin demand can be derived.

Figure 2A:
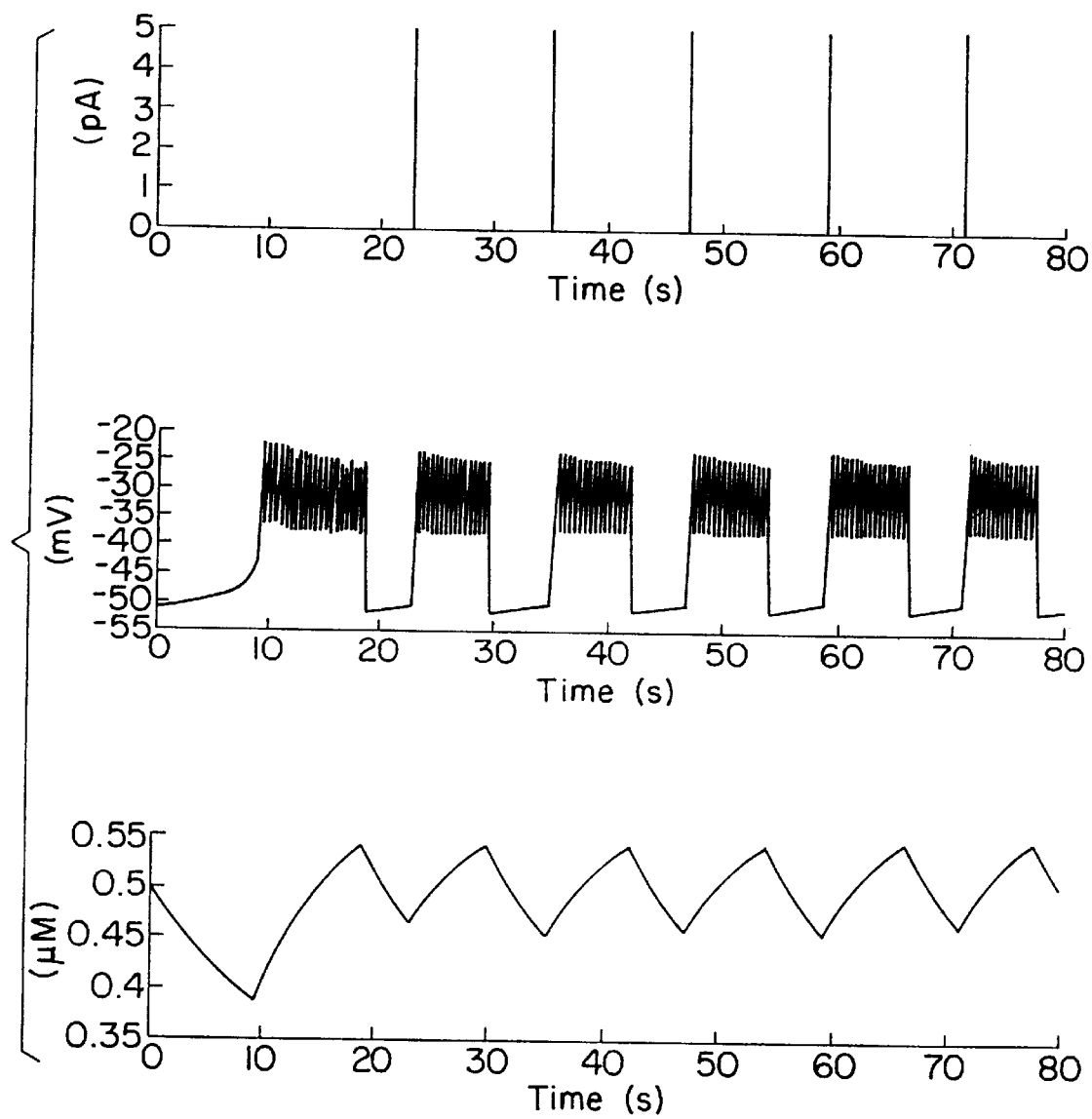
FIG. 2A is a diagram illustrating the effect of stimulation delivered so as to initiate earlier depolarization bursts by the pancreatic islets, as well as the corresponding variation of intra-cellular calcium.

Referring now to FIG. 2A, there are shown three sets of timing diagrams illustrating the effect of stimulating beta cells so as to increase insulin production, in this case on a 12 second repetition interval where capture is produced by each stimulus. The first burst illustrated is a spontaneous burst. The second burst is evoked by a stimulus delivered before a next burst spontaneously occurred, resulting in a shortened repolarization duration. Each burst thereafter is triggered by a stimulus pulse; note that the length of each depolarization burst plateau is substantially the same as for the spontaneous burst, but the repolarization durations are shorter, resulting in a larger duty cycle. The lower timing curve illustrates variation of intra-cellular calcium, showing that such calcium rises as a function of burst activity. It is the rising in calcium which, as discussed above, triggers insulin secretion, and consequently the narrowing of the repolarization duration relative to the depolarization duration results in increased insulin production.

Figure 2B:
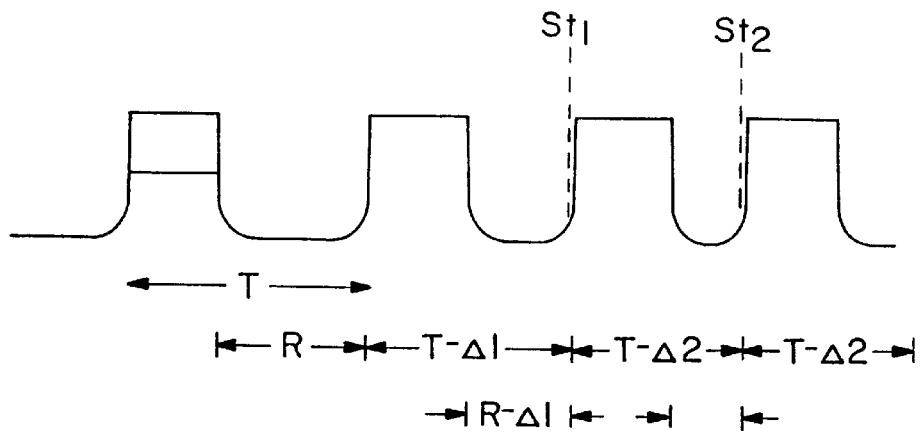
FIG. 2B is a further diagram illustrating stimulus timing calculated to increase the relative amount of burst activity and the consequentially increased insulin production.

FIG. 2B is a schematic timing diagram illustrating the timing of stimulus pulses delivered to the pancreatic islets, in order to increase their insulin production. The first two bursts are illustrated as spontaneous bursts; T is the low frequency cycle period, while R is illustrated as the time from the end of one burst to the onset of the next burst. A first stimulus $St_1$ is illustrated as being delivered before the anticipated spontaneous onset of the next burst. Thus, the period from the onset of the second spontaneous burst to the first stimulus-evoked burst is $T-\Delta_1$, and the time from the end of the second spontaneous burst to the $St_1$ is $R-\Delta 1$. In this case, the second stimulus pulse is shown as being delivered after a further decreased cycle time of $T-\Delta_2$, corresponding to a shortened repolarization interval of $R-\Delta_2$. Thus, control can be effected either by timing out a stimulus interval from the last stimulus pulse, or from the end of the last burst plateau. The stimulus rate can be increased relative to the spontaneous rate in any programmed manner, e.g., by a single step to a higher rate, or by ramping up to a higher rate.

Figure 3:
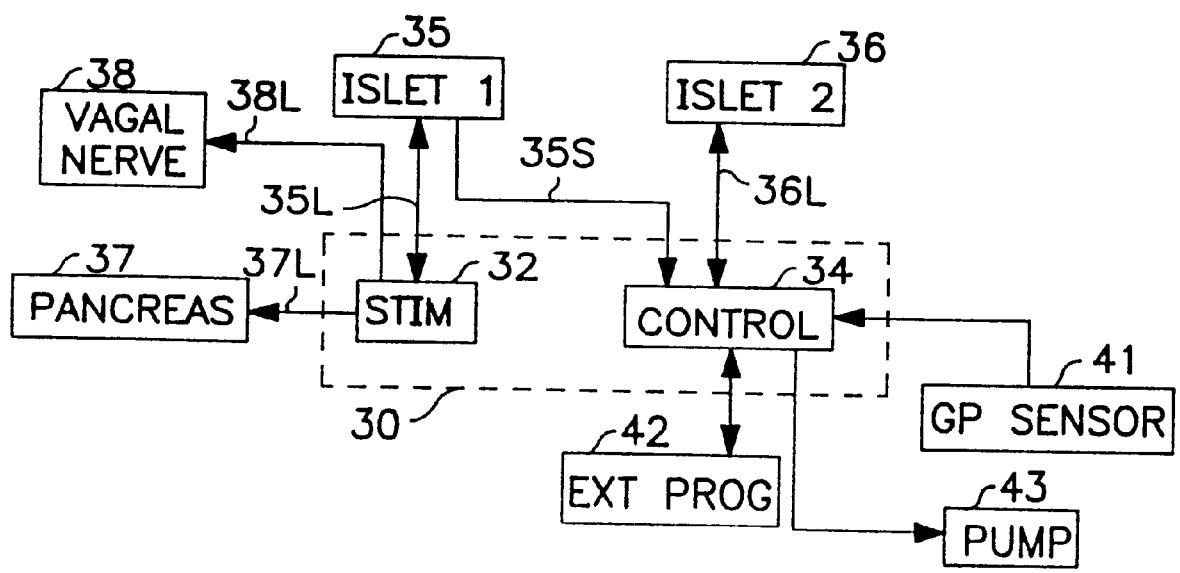
FIG. 3 is a schematic diagram of a system in accordance with this invention for generating and delivering stimulus pulses to an islet transplant, to the patient's pancreas or to the patient's vagal nerve, for controlling insulin production.

Referring now to FIG. 3, there is shown a schematic block diagram of a system in accordance with this invention. An implantable device 30 is shown having two primary components, a stimulus generator 32 and a control block 34. Stimulus generator 32 is preferably a controllable electronic stimulus generator. Control block 34 contains all of the control circuitry, including circuitry for carrying out logic and timing functions. Control 34 preferably contains a microprocessor and associated memory for storing respective algorithms used in carrying out the invention. Stimulus generator 32 produces stimulus output pulses under control of block 34, which are connected to the pancreatic beta cells positioned at predetermined patient locations. It is to be noted that the output stimuli from generator 32 are delivered across electrode pairs to produce electric field stimuli at the site of the beta cells. As illustrated, an islet transplant 35 receives stimulus pulses from stimulus generator 32 by lead 35L. The pancreas, illustrated at 37, can be stimulated by pulses delivered on lead 37L. Further, pancreatic activity can be controlled by delivering stimulus pulses to the vagal nerve 38 over lead 38L. Further included within the system may be a glucose sensor 41, such as means for receiving and analyzing EKG signals to determine a measure of blood glucose level, as set forth in U.S. Pat. No. 5,741,211, assigned to the assignee of the present invention incorporated herein by reference. Alternately, the electrical activity of a second islet, illustrated at 36, can be monitored through lead 36L, to determine a measure of blood glucose. Also, as discussed in concurrently filed application Ser. No. 08/876, 738, incorporated herein by reference, glucose can be monitored by stimulating either the pancreas or transplant 35 to evoke synchronized bursts which in turn are processed to obtain a measure of blood glucose. Further, an external programmer 42 may be used for transmitting to control block 34 an externally obtained a measure of blood glucose, e.g., as obtained by conventional glucose blood sampling. External programmer 42 is also used for inputting a signal to device 30 to indicate the start of a glucose load when a patient commences eating, and for other programming functions, e.g., resetting stimulation parameters. Insulin response may also be effected by controlling insulin ejection from a pump 43.

Figure 4A:
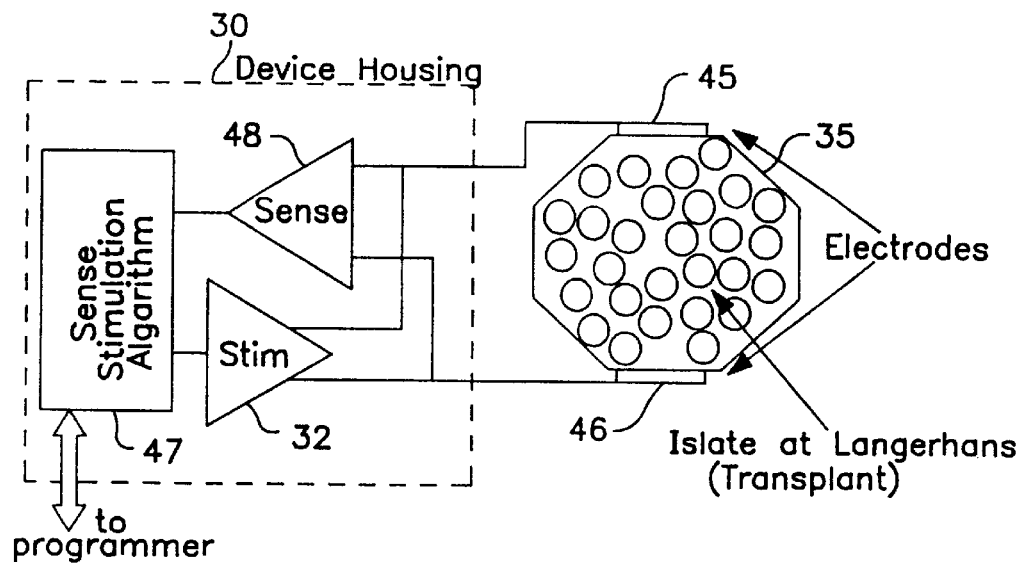
FIG. 4A is a schematic diagram showing an arrangement for sensing and stimulating across a transplant.

Referring now to FIG. 4A, there is shown a schematic diagram illustrating in simplified detail a system for sensing electrical activity across a transplant 35 of islets of Langerhans, and stimulating such transplant to control changes in insulin production. Stimulus pulses from Stim generator 32 are connected across the electrodes 45, 46 while the electrical activity of the transplant is sensed by sense amplifier 48. A sense stimulation algorithm is indicated at 47, which is contained in control block 34 as illustrated in FIG. 3. In such a system, a measure of blood glucose can be obtained simply by sensing signals from electrodes 45, 46 in sense circuit 48 and processing them with algorithm 47. During the sensing operation stimulator 32 may be utilized to provide depolarization stimulus pulses to the transplant, timed to synchronized bursts for the purpose of enhancing sensing. Additionally, algorithm 47 may control generator 32 to produce stimulus pulses timed to increase insulin production, as discussed in reference to FIG. 2B above.

Figure 4B:
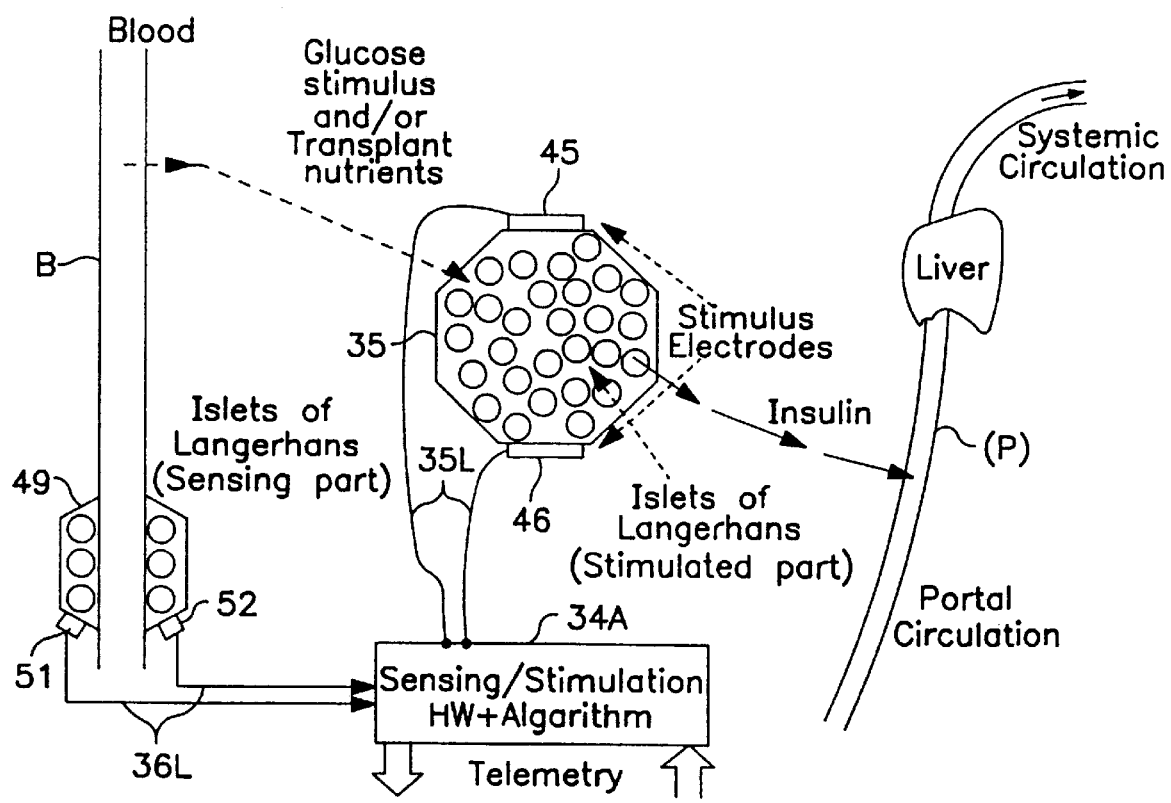
FIG. 4B is a schematic diagram illustrating the use of two islet transplants, one for sensing and one for insulin production.

Referring now to FIG. 4B, there is shown a schematic diagram illustrating the use of two transplants, to provide separate glucose sensing and insulin production. As illustrated, a first transplant 35 is shown, which is used only for stimulation in order to increase its own production. Under the control of sensing/stimulation algorithm 48, stimulus pulses are delivered across lead 35L to electrodes 45 and 46, as illustrated also in FIG. 4A. As illustrated, glucose information is transmitted from the patient's blood stream (B) along with transplant nutrients, to the transplant 35. Insulin from transplant 35 is produced with an appropriate delay in accordance with the above-discussed insulin kinetics, under control of algorithm 34A. The insulin passes to portal circulation (P) whence it passes through the liver to the systemic circulation. A second transplant of islets of Langerhans, for sensing, is located close to the blood stream, as illustrated diagrammatically at 49. Electrical activity from this transplant is sensed at electrodes 51, 52, and transmitted through lead 36L to be operated on at algorithm block 34A. The algorithm may, as indicated, be in communication with an external programmer through telemetry. By this arrangement, a smaller volume transplant can be positioned for more optimum sensing, while a larger volume transplant can be positioned for insulin production.

Figure 5A:
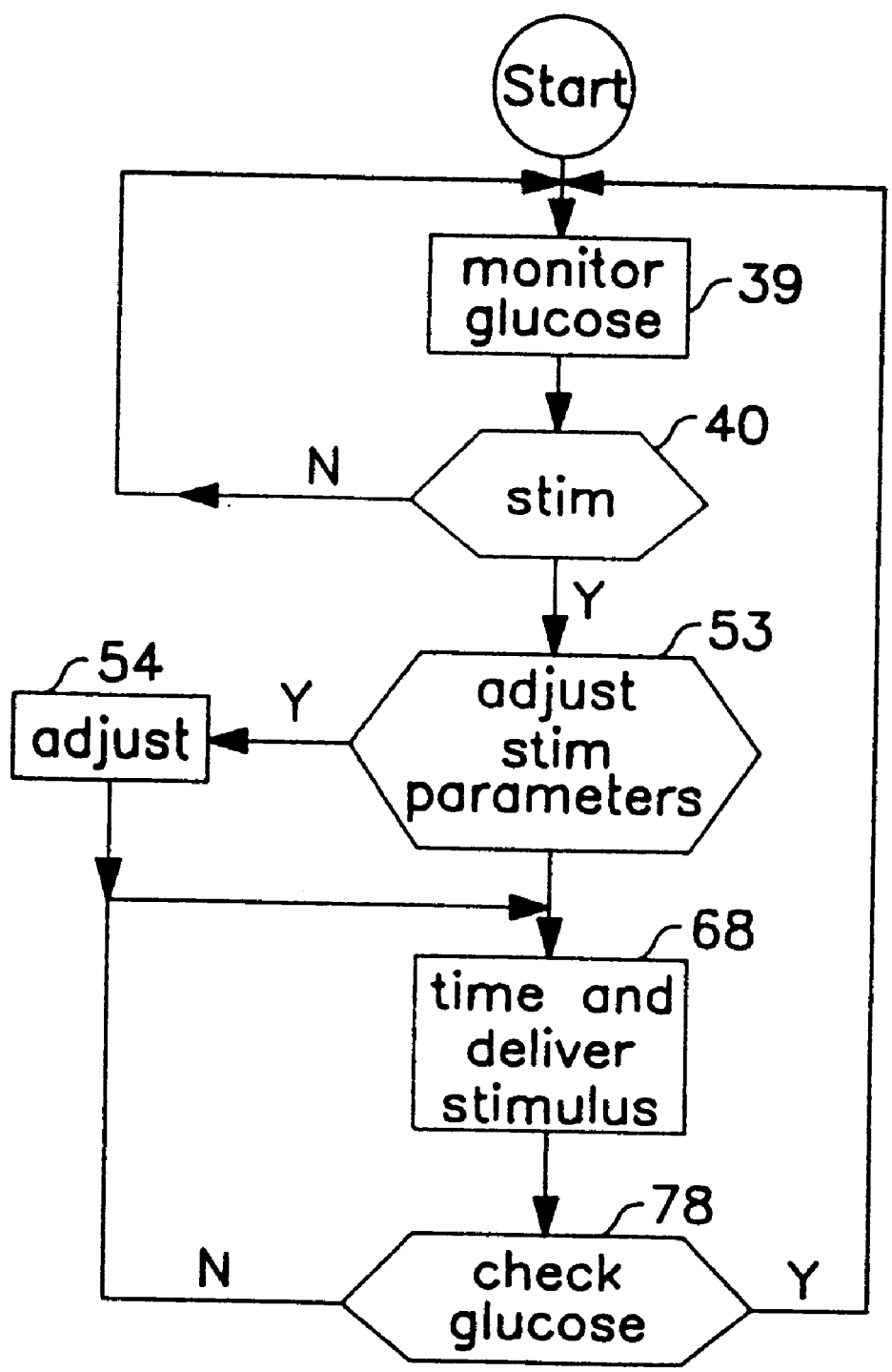
FIG. 5A is a flow diagram of steps carried out in a preferred embodiment of monitoring blood glucose level and then stimulating to increase insulin production when the patient needs more insulin.

Referring now to FIG. 5A, there is shown a flow diagram of the summary steps taken in a preferred embodiment of the invention which includes continually monitoring patient blood glucose level and stimulating accordingly to vary production of insulin. At 39, the system monitors glucose. This can be done by any one of several alternate ways. Thus, the spontaneous electrical activity of the transplant, or the pancreas, can be monitored, and glucose determined as a function of the depolarization burst duration. Alternately, the patient EKG can be monitored, and glucose level determined therefrom. At 40, a determination is made as to whether the glucose level indicates that increased insulin is wanted, thereby determining whether stimulation should be started. If no, the routine continues to monitor glucose. But, if the answer at 40 is yes, the routine goes to 53 and determines whether to adjust the stimulation parameters, e.g., the rate. If yes, the adjustment is made at block 54, e.g., rate is increased to be a predetermined incremental rate above the spontaneous rate. At 68, the stimulus is timed and delivered, after which the routine determines at 78 whether glucose should be checked. For example, glucose can be checked every 1 or 2 minutes. If glucose is not to be checked, the routine returns to 68 for the next stimulus; if glucose is to be checked, the routine returns to block 39.

Figure 5B:
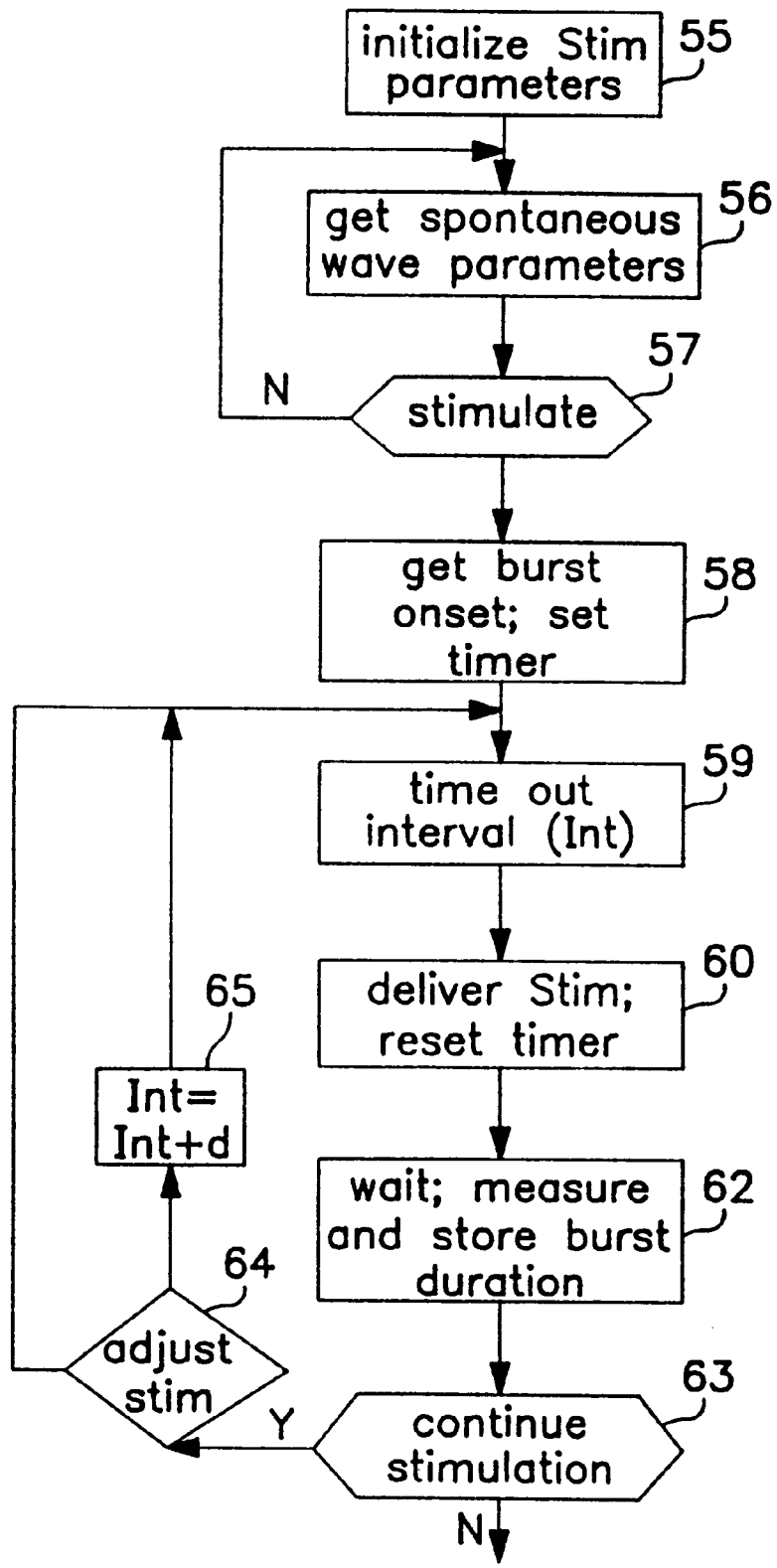
FIG. 5B is a flow diagram illustrating steps for generating stimulus pulses timed for stimulating pancreatic beta cells in order to increase insulin production.

Referring now to FIG. 5B, there is illustrated a flow diagram showing the primary steps for timing and delivering stimulus pulses to increase insulin production at a location containing a pancreatic cell, i.e., where an islet transplant is located, or directly at the pancreas. Alternately, as discussed above, the stimulus pulses can be delivered to the vagal nerve, for indirect stimulus of the pancreas. At 55, the stimulation parameters are initialized, e.g., threshold voltage and current. At 56, the algorithm waits and gets spontaneous slow wave parameters. This may be done by waiting a predetermined number of slow wave cycles, so as to obtain both a measure of the burst duration and the slow cycle rate. At 57, a decision is made as to whether or not to stimulate so as to increase insulin. Thus, the average burst duration or duty cycle is compared to a reference value to make this determination. If the decision is not to stimulate, the routine simply loops back and continues monitoring slow wave parameters. When the decision at 57 is yes, the routine goes to 58 and waits for the spontaneous burst onset, at which time it sets a timer to time out interval T-$\Delta$1 (as illustrated in FIG. 2B). When the interval is timed out, at 60 the stimulus is delivered, and the timer is reset. The timer may be reset to the same interval, or a shorter interval, depending on the algorithm. At 62, the system waits for the end of the burst, and then measures and stores the burst duration. This enables the system to monitor induced increases in delivered insulin. At 63, a decision is made as to whether to continue stimulation, based upon blood glucose level. Although not shown in block 63, blood glucose level is suitably continuously monitored to provide this information. If the decision is to continue stimulation, the routine goes to 64 and determines whether to adjust stimulation. Thus, the stimulation rate may be increased or decreased, as desired. If stimulation is to be adjusted, at block 65 the interval is changed by an increment d, which may be plus or minus. Following this, the routine goes back to 59 and continues the stimulation. Whenever a decision has been made not to continue stimulation, the routine exits.

Figure 6:
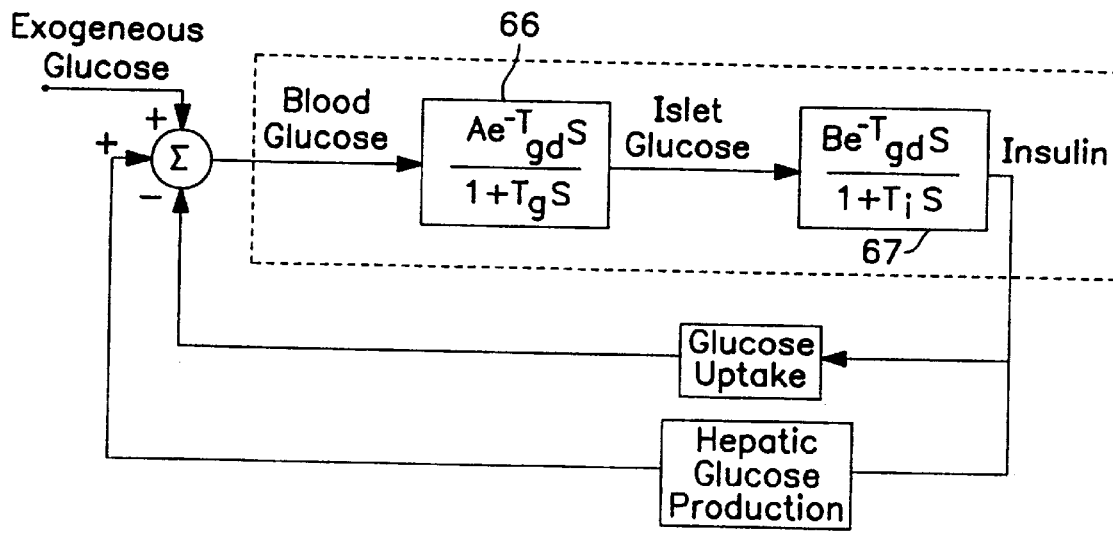
FIG. 6 is a model of glucose dynamics, illustrating insulin and blood dynamics, and indicating the nature of delays in insulin production following glucose load signals.

Referring now to FIG. 6, there is illustrated a first order model describing the dynamics of glucose diffusing from the blood stream into the intra-peritoneal cavity towards an implanted encapsulated islet graft, and the diffusion of produced insulin towards the systemic circulation. The formula of block 66 illustrates parameters $T_{gd}$ and $T_g$ which describe the lag-time and time-constant for blood glucose to reach and spread over encapsulated islets. Thus, the blood glucose signal is derived from exogenous glucose, from hepatic glucose production (through the liver), and decremented by glucose uptake due to insulin production. Block 66 illustrates the delay due to blood glucose kinetics upon receipt of the glucose signal at the site of the transplant. Block 67 contains parameters $T_{id}$ and $T_i$ which relate to the diffusion process whereby insulin produced by the transplant reaches the systemic blood flow. The time parameters are suitably inputted into algorithm 48 (FIG. 4B) for calculation of a suitable stimulation profile in responding to an input signal from transplant 49 which calls for an increase in insulin. The stimulation profile controls the timing of when stimulus pulses are delivered, as well as the intensity, e.g., rate increase of delivered stimuli.

Figure 7A:
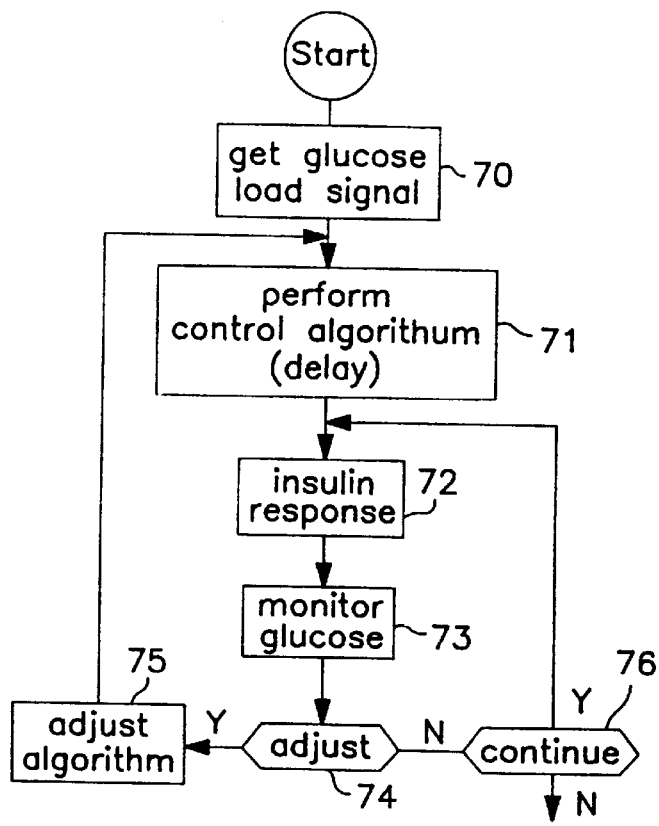
FIG. 7A is a flow diagram illustrating the incorporating a timing pattern of delays into the system response to a glucose load.

Referring now to FIG. 7A, there is shown a simplified flow diagram of the primary steps taken in responding with an appropriate stimulation pattern to a glucose signal calling for increased insulin production. In general, the glucose signal can come either from a transplant 49, or it may be an externally generated signal indicating the start of food intake. Alternately, as discussed further in connection with FIGS. 7B, the initiation of a response may be derived from a sensed signal indicative of the stomach or the duodenum filling. Of course, the stimulation pattern will vary depending upon the nature of the signal. At 70, the glucose load sensor is monitored for receipt of a glucose load signal. At 71, in response to a load signal, the control algorithm is initiated and generates an appropriate stimulation profile. At 72, the insulin response is carried out, i.e., insulin is provided either by controlling ejection from an insulin pump, or increased insulin is produced by stimulation. After cessation of the stimulation profile which enhances insulin production, glucose is monitored, as shown at 73. At 74, the glucose level is analyzed, and it is determined whether the control should be adjusted. If yes, the control algorithm is adjusted at 75, following which the routine returns to 71 for control by the adjusted algorithm. If no adjustment is called for, at 76 it is determined whether insulin response is to continue. If yes, the routine goes back to block 72 and continues the programmed response. Thus, the algorithm provides for an appropriate delay depending upon the source of the glucose load signal, and for ongoing adjustment of the indicated insulin response as a function of monitored glucose blood level.

Figure 7B:
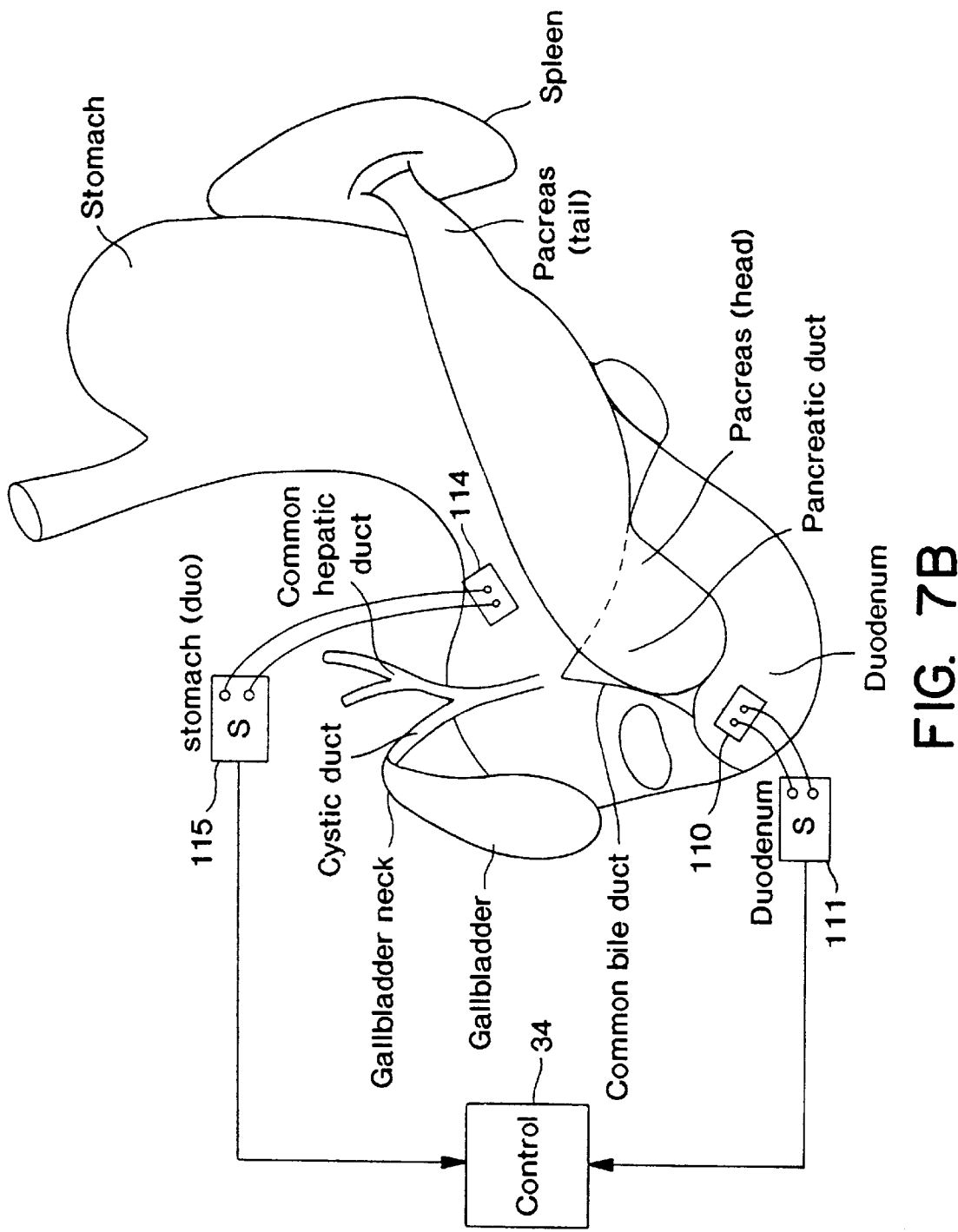
FIG. 7B is a schematic illustration of an embodiment for sensing start of a glucose load in the duodenum or the stomach.

Referring to FIG. 7B, there is shown a schematic diagram illustrating sensor arrangements for obtaining glucose load signals from the duodenum or the stomach. Electrodes 110 are positioned in or on the duodenum, and connected to sensor input 111. The signals from block 111, which carry data relating to food intake, are coupled to control block 34 for use in initiating a stimulus pattern. Likewise, in the alternative, electrodes 114 are positioned in or on the stomach, and provide signals that are processed at sensor input 115. These signals also carry data indicative of the stomach filling, and thus start of a glucose demand, and are coupled to control 34.

Referring now to FIG. 8A, there are illustrated timing diagrams of stimulation which is programmed to react to hypoglycemia, or incipient hypoglycemia, by inhibiting insulin production by pancreatic insulin-producing beta cells, either in transplants of islets of Langerhans, or directly in the pancreas. The center diagram (2) shows a first spontaneous burst of a first duration. After a shorter repolarization internal, a next burst starts, which is interrupted by a stimulus (diagram 1) timed to shorten the burst durations. As seen in the lower diagram (3), this results in a decrease of intra-cellular calcium, and a resultant decrease in insulin secretion. Accordingly, insulin production is inhibited by timing out a shortened internal following a burst onset, and delivering an above-threshold stimulus at time-out, which stimulus terminates the depolarization and commences repolarization.

Figure 8B:
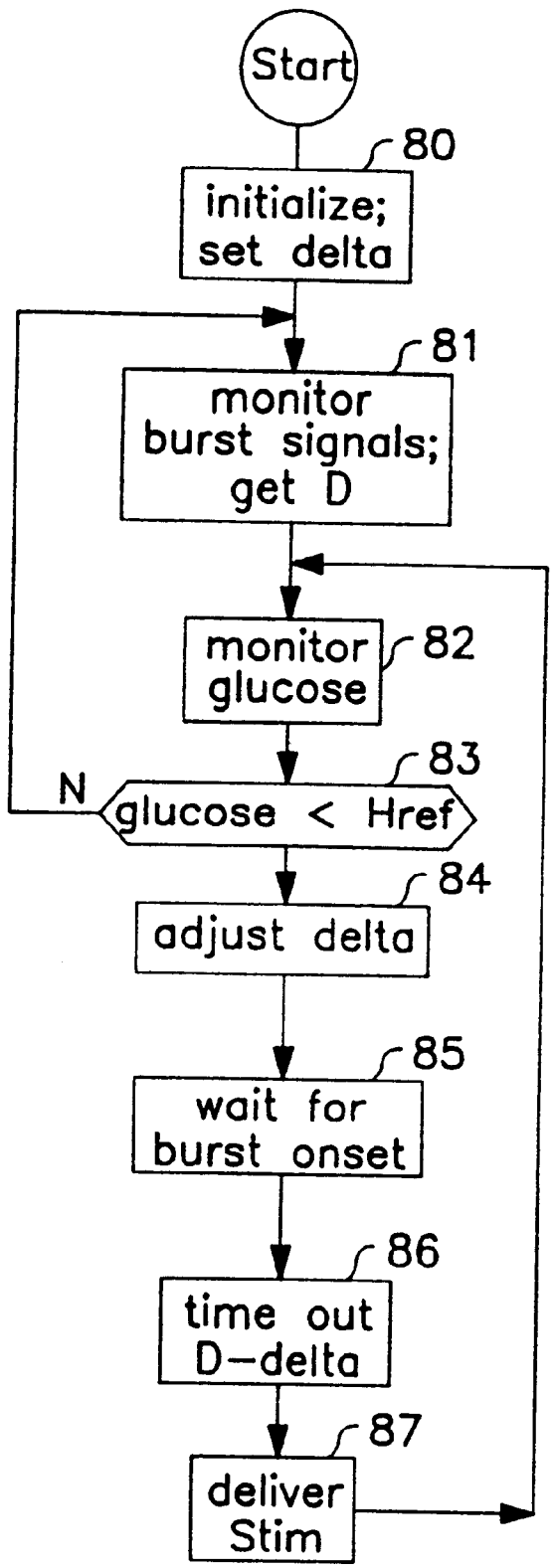
FIG. 8B is a flow diagram illustrating the primary steps taken in a sub-routine responsive to hypoglycemia for stimulating so as to inhibit insulin production.

Referring now to FIG. 8B, there is shown a flow diagram illustrating the primary steps taken in a sub routine for inhibiting insulin production, in accordance with this invention. At 80, the routine is initialized, which includes setting the time decrement "delta". At 81, spontaneous signals are monitored, and the burst duration (D) is determined. At 82, glucose is monitored, and at 83 the glucose level is compared to a predetermined reference, H ref, which represents a level below which the patient is hypoglycemic, or dangerously close thereto. If the glucose level is less than H ref, the routine loops back to 81. If glucose is greater than H ref, the routine proceeds to 84 and adjusts delta, depending on the urgency for reducing insulin production. Alternately, or additionally, the time rate of change of blood glucose level can be determined as an indictor, or predictor, of hypoglycemia. At 85, the system waits for the next burst onset, and then at 86, the interval D-delta is timed out. At time out, the stimulus pulse is delivered, as indicated at 87. The stimulate step at 87 may involve one or more burst cycles, with a stimulus delivered at D-delta after onset of each burst. Thus, steps 85, 86 and 87 can be repeated a programmable number of times, e.g., 10 or 20 times. After the stimulate episode, the route returns to 82, where glucose is again monitored.

Figure 9:
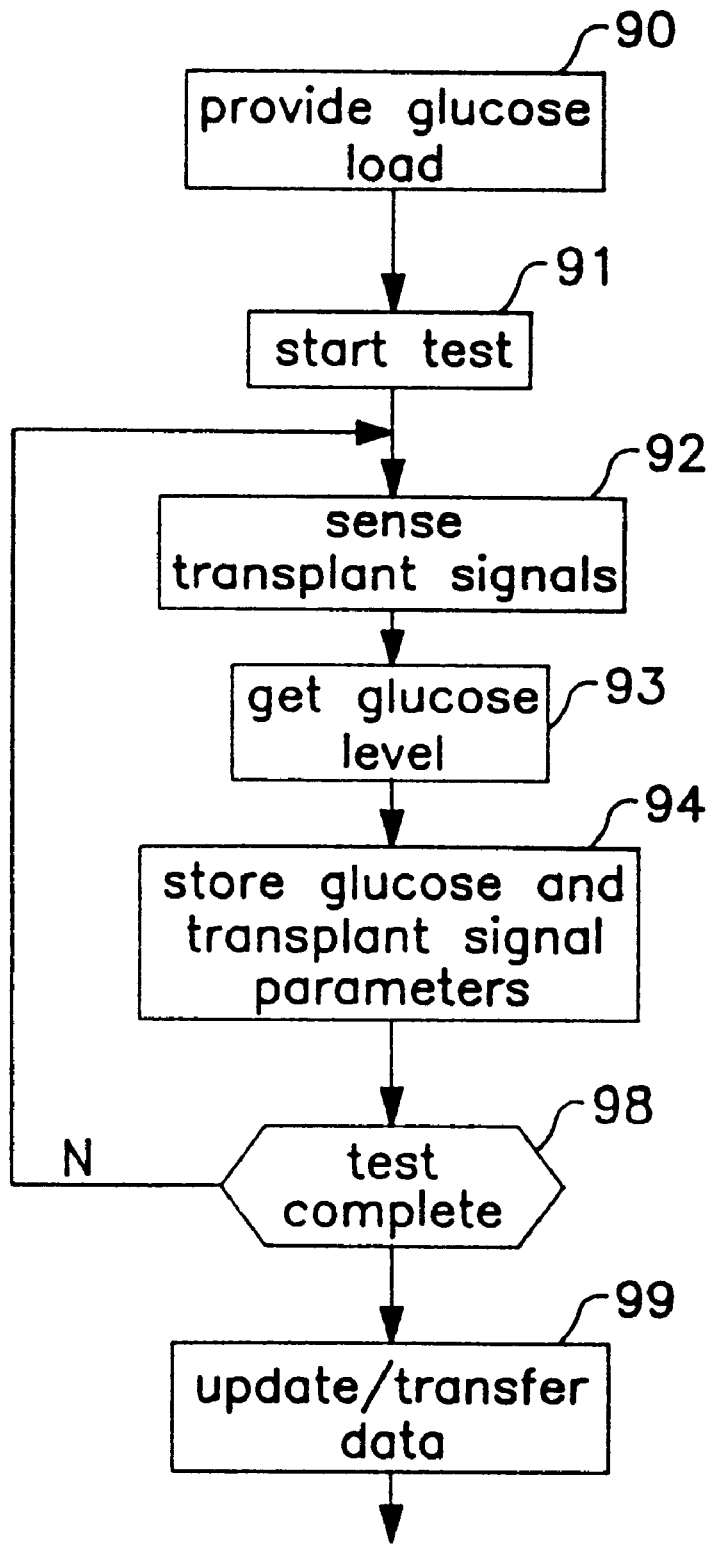
FIG. 9 is a flow diagram showing the primary steps of an embodiment of this invention for monitoring the functionality of an islet transplant.

Referring now to FIG. 9, there is shown a flow diagram of the primary steps taken in monitoring the functionality of a transplant, in accordance with this invention. At 90, the patient starts to eat, and transmits a glucose load signal to the implanted device by any suitable external programmer. At 91, the functionality test is started, in response to the load signal. At 92, electrical signals from the transplant activity are sensed, from which one or more pertinent signal parameters, e.g., burst duration, is derived. At 93, glucose is measured, suitably by another internal sensor. At 94, the corresponding glucose and transplant parameter data is stored. If, at 98, the test is not complete, the routine loops back to 92. Test completion may be programmed for a pre-determined time period, e.g., 15–30 minutes following food intake. Further, the data storing step at 94 may include any suitable processing and data compression. After the test has been completed, the data may be down loaded to the external programmer, for evaluation. Alternatively, the data can be held for further compiling with data from subsequent test, as indicated at block 99.

There have thus been disclosed several embodiments of the system and method of this invention. The feature of stimulating to increase or decrease insulin production may be practiced on a transplant of islets, or directly on the pancreas. As claimed, the stimulation of pancreatic beta cells refers to stimulating such cells in the patients' pancreas, or wherever a transplant is located.

Figure 10:
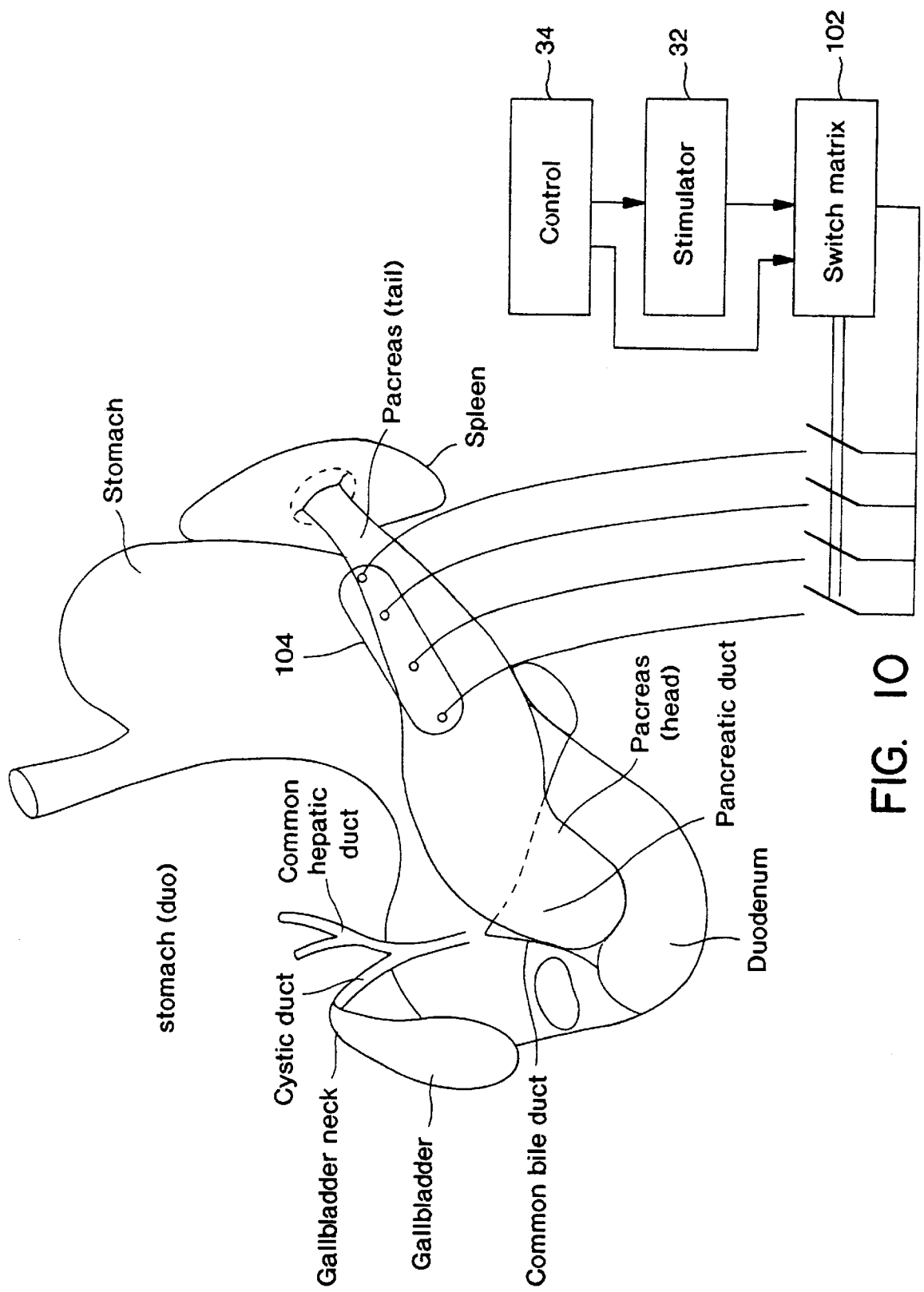
FIG. 10 is a schematic diagram illustrating a subsystem for switching stimulation to different electrode pairs in or on the pancreas.

Referring now to FIG. 10, there is shown a schematic diagram illustrating an embodiment for switching the delivered stimuli to respective different pairs of electrodes positioned in the pancreas. Switching the site of stimulation provides a way to deal with the recognized "overworked beta cell" problem. As is known, the synthesis of insulin is normally regulated within the beta cell by stimulating the cell with glucose, which stimulates exocytosis of insulin. Electrical stimulation, or hypoglycemic agents act on the ATP gated potassium channel and promote only exocytosis of insulin, not insulin synthesis. Every beta cell has at least two known stores of insulin, i.e., insulin and pro-insulin. It is the former that is ready for direct release and is depleted by electrical or chemical stimulation. This can cause a supply-depletion imbalance, which in type II diabetes leads to overworked beta cells. Switching the islets which are stimulated can lessen this problem. As illustrated, control 34 provides control switches to adjust switch matrix 102 so as to deliver the stimuli from generator across respective pairs of electrodes 104 positioned in or on the pancreas. The system can be programmed to cause switching periodically, e.g., weekly, daily, or even for each meal.

Figure 11:
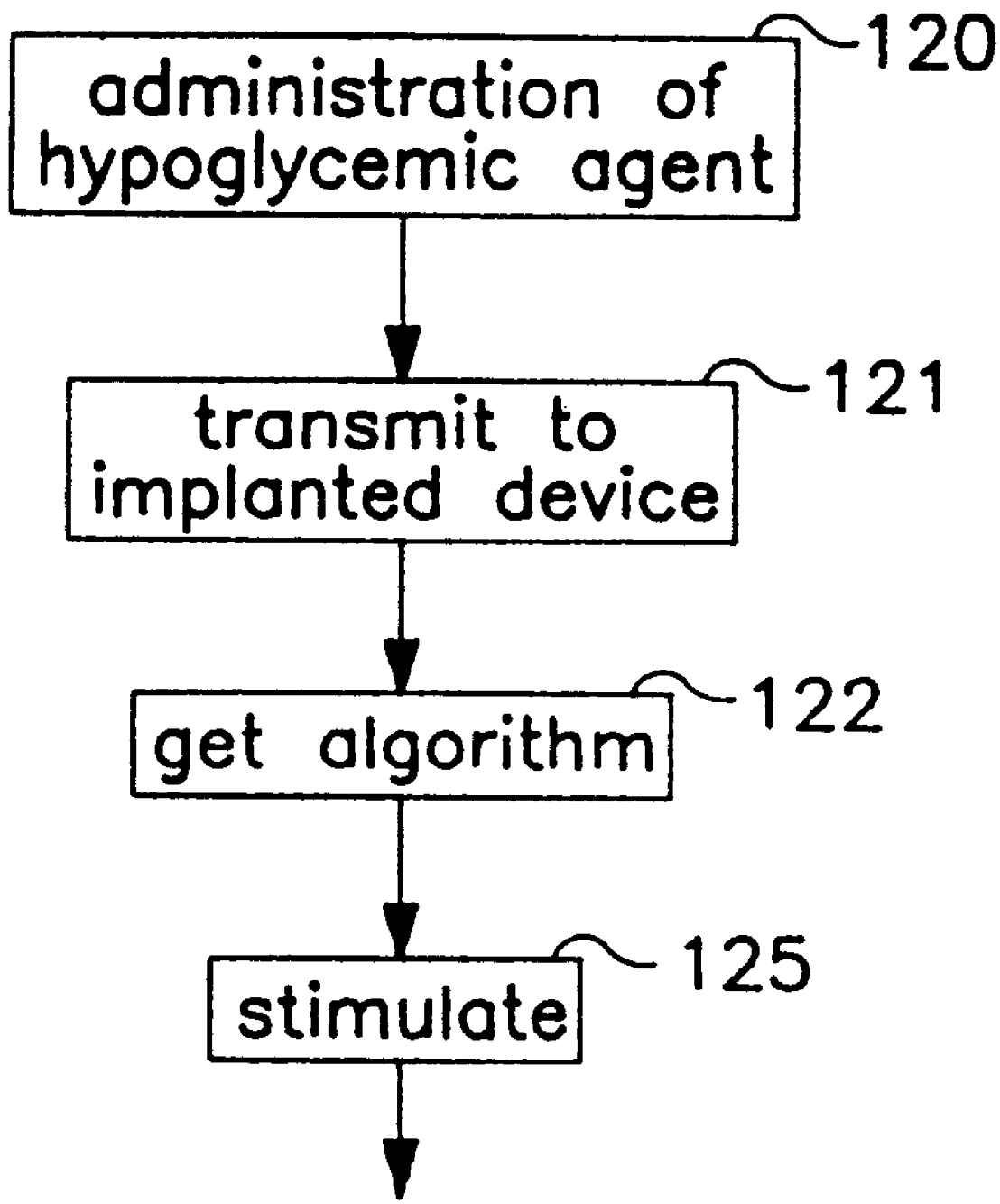
FIG. 11 is a flow diagram illustrating the primary steps of combining the taking of a hypoglycemic agent with stimulation of pancreatic beta cells, in accordance with this invention.

In another embodiment, stimulation of the pancreas, or an islet transplant, is combined with the patient taking a hypoglycemic medication, e.g., an agent from the class of biguanide derivatives, sulfonylureas agents or alpha-glucosidase inhibitors. By combining the two steps substantially concurrently, there can result an increase of insulin release greater than by either application alone. Referring to FIG. 11, the patient takes the hypoglycemic agent, as shown at 120, and then transmits a signal to the implanted device with an external programmer, as shown at 121. The device detects the administration of the agent, and at 122 calls upon a pre-loaded algorithm that corresponds to the agent. Thus, the agent may effect a characteristic pattern, and the stimulation algorithm is chosen to provide a complementary pattern of stimulation, e.g., stimulating concurrently with the characteristic response to the agent. Under control of the algorithm, the stimulation is carried out as illustrated at 125. Alternately, stimulation in accord with this invention can be used to cover peaks after meals, while the basal need is covered by oral hypoglycemic medication.

What is claimed is:

1. A system for stimulating pancreatic beta cells located at a predetermined patient location for the purpose of increasing insulin production by such beta cells, comprising:
   a controllable stimulus generator for generating stimulus pulses;
   delivery means for delivering said stimulus pulses to said cells at said location; and
   control means for controlling said generator to generate stimulus pulses timed to increase the rate of insulin production by said beta cells.

2. The system as described in claim 1, wherein said control means comprises sensing means for sensing spontaneous depolarization bursts of said beta cells, timing means for developing timing signals corresponding to said bursts, and control signal means for generating control signals for initiating a stimulus pulse as a function of said timing signals.

3. The system as described in claim 2, wherein said control signal means comprises means for determining the rate of said spontaneous bursts and for generating said control signals at a rate greater than said burst rate.

4. The system as described in claim 2, wherein said control signal means comprises means for determining the end of each burst evoked by a delivered stimulus pulse, and means for generating a next control signal at a predetermined time following each said burst end.

5. The system as described in claim 1, wherein said patient has a transplant of islets of Langerhans at said location, and said delivery means comprises lead means for delivering said stimulus pulses to said transplant.

6. The system as described in claim 1, wherein said delivery means comprises lead means for delivering said stimulus pulses to said patient's pancreas.

7. The system as described in claim 1, wherein said delivery means comprises lead means for delivering said stimulus pulses to said patient's vagal nerve, thereby evoking pancreatic beta cell depolarization bursts.

8. The system as described in claim 1, wherein said patient has a transplant of islets of Langerhans positioned at a second location close to a patient bloodstream, sensing means for sensing electrical activity of beta cells of said islets at said second location, glucose means for determining an increase in blood glucose as a function of said sensed islet electrical activity, and means for initiating generation of said stimulus pulses in response to a sensed increase in glucose.

9. The system as described in claim 1, comprising means positionable external to said patient's body for initiating generation of said stimulus pulses.

10. The system as described in claim 9, further comprising program means for controlling said stimulator to generate stimulus pulses in accord with a predetermined program over at least a given period to time.

11. The system as described in claim 1, comprising implantable measure means for obtaining a measure of patient blood glucose, and response means for controlling generation of said stimulus pulses as a function of said measure.

12. The system as described in claim 11, wherein said means comprises means for controlling said stimulus generator to generate synchronizing pulses timed to evoke depolarization bursts in said beta cells.

13. The system as described in claim 11, wherein said patient has a transplant of islets of Langerhans containing beta cells, and wherein said measure means comprises means for determining said measure from the electrical activity of said transplant beta cells.

14. The system as described in claim 1, comprising glucose means for determining a measure of patient glucose, and adjust means for adjusting the timing of delivery of said stimulus pulses as a function of said glucose measure.

15. The system as described in claim 14, comprising means for determining when said glucose measure is below a predetermined level, thus indicating hypoglycemia, and wherein said adjust means comprises means responsive to indicated hypoglycemia for controlling said stimulus generator to time said stimulus pulses so as to decrease beta cell depolarization burst durations.

16. A system implantable in a patient for detecting and responding to patient hypoglycemia, comprising:
   glucose means for monitoring patient blood glucose;
   means for determining when said monitored blood glucose indicates hypoglycemia;
   stimulus means for generating stimulus pulses and delivering said pulses to a selected patient location containing insulin-producing pancreatic beta cells; and
   control means for controlling the timing of said stimulus pulses so as to decrease the insulin secretion of said beta cells.

17. The system as described in claim 16, wherein said control means comprises means for determining parameters of spontaneous depolarization bursts of said beta cells, and timing means for timing delivery of said stimulus pulses to shorten the durations of the cell depolarization bursts.

18. The system as described in claim 17, wherein said patient has encapsulated islets of Langerhans at said location, and said stimulus means comprises lead means for delivering said stimulus pulses to said islets.

19. The system as described in claim 17, wherein said stimulus means comprises lead means for delivering said stimulus pulses to the patient's pancreas.

20. An implantable system for sensing electrical activity of pancreatic beta cells and stimulating said beta cells to promote increased insulin production therefrom, comprising:
   glucose means for continually obtaining a measure of patient blood glucose level, and determining from said measure when increased insulin production is indicated; and
   stimulus means responsive to an indication of increased insulin production for stimulating said beta cells with pulses timed to increase the duty cycle of depolarization bursts of said cells.

21. The system as described in claim 20, wherein said patient has a transplant of islets of said beta cells, and said glucose means comprises first sensing means for sensing activity of said transplant cells, and determining means for determining said measure of blood glucose from said sensed activity.

22. The system as described in claim 20, wherein said glucose means comprises means for sensing patient EKG signals and for obtaining said glucose measure from said signals.

23. The system as described in claim 20, wherein said glucose means comprises means for sensing spontaneous beta cell activity in said patient's pancreas and for obtaining said glucose measure from said sensed cell activity.

24. The system as described in claim 20, further comprising means for receiving an external communication carrying glucose data pertaining to start of glucose load or patient blood glucose level.

25. The system as described in claim 24, comprising control means for controlling said stimulus means to respond to a glucose load with a predetermined timed response.

26. The system as described in claim 25, wherein said control means comprises software algorithm means for introducing compensation reflective of patient glucose kinetics.

27. The system as described in claim 20, wherein said patient has a transplant of islets of beta cells, and further comprising:

glucose data means for storing data representative of obtained measures of blood glucose level;

burst means for sensing at least one predetermined parameter of the spontaneous depolarization bursts of said transplant and storing data representative of same; and functionality means for analyzing said stored glucose and parameter data and determining therefrom a measure of transplant functionality.

28. A system for delivering a timed insulin response to start of food intake by a patient, comprising:

intake means for determining when a patient has commenced and/or completed food intake;

algorithm means initiated by said intake means for determining a timed insulin production response following a said food intake; and insulin means for increasing insulin in said patient according to said timed insulin response.

29. The system as described in claim 28, comprising an implantable device housing said intake means and said insulin means, said implantable device further comprising receiver means for receiving an externally generated intake signal.

30. The system as described in claim 29, wherein said insulin means comprises a controllable insulin pump.

31. The system as described in claim 29, wherein said insulin means comprises stimulus means for stimulating the patient's pancreas with pulses timed to increase pancreatic insulin production.

32. The system as described in claim 29, wherein said patient has a transplant of islets of Langerhans, and said insulin means comprises stimulus means for stimulating said transplant with pulses timed to increase insulin production by said islets.

33. The system as described in claim 29, comprising glucose monitoring means for obtaining a measure of blood glucose, and further comprising adjust means for adjustably controlling said insulin means to produce insulin at a rate which is a function of said glucose measure.

34. The system as described in claim 33, wherein said adjust means comprises means for controlling said insulin means to decrease insulin production in response to an obtained glucose measure which is below a predetermined reference which represents hypoglycemia.

35. The system as described in claim 28, wherein said algorithm means comprises compensation means for introducing a compensated insulin response which is based upon insulin and glucose dynamics.

36. A system for monitoring functionality of an islet transplant in a patient, comprising:

glucose means for determining and storing representations of patient blood glucose level;

sensing means for sensing electrical activity of said transplant and for storing representations of said activity corresponding timewise with said glucose representations; and diagnostic means for providing diagnostic data based on said stored glucose and activity representations.

37. The system as described in claim 36, wherein said glucose means and said sensing means periodically store said representations, and said diagnostic means comprises means for processing said representations to provide data representative of transplant functionality over at least a predetermined period of time.

38. The system as described in claim 36, further comprising intake means for determining when said patient has intaken food, and control means for controlling said glucose means and said sensing means to obtain said representations following patient intake of food.

39. The system as described in claim 38, wherein said control means further comprises algorithm means for timing the operation of obtaining said representations.

40. A method of increasing insulin production by stimulating insulin-producing islets in a patient, comprising:

sensing spontaneous electrical signals of said islets and determining at least one predetermined parameter relating to the depolarization bursts of said signals; and delivering stimulus pulses to said islets so as to increase the time duration of said bursts relative to the islet repolarization intervals.

41. The method as described in claim 40, further comprising positioning a first relatively large volume transplant of said islets in the patient at a first location and positioning a second relatively smaller volume transplant of said islets at a second location close to a patient bloodstream, and wherein said sensing comprises sensing signals of said second transplant and said delivering comprises delivering stimulus pulses to said first transplant.

42. The method as described in claim 40, further comprising monitoring patient blood glucose, and stopping said delivering step whenever said blood glucose indicates a hypoglycemic condition.

43. The method as described in claim 42, further comprising delivering stimulus pulses to said islets timed to decrease the time duration of said bursts relative to the islet repolarization intervals, thereby decreasing insulin production.

44. A method of responding to patient food intake by delivering insulin in accord with a predetermined time response, comprising:

determining when a patient has commenced food intake;

processing an algorithm to determine a timed response as a function of patient glucose and insulin dynamics; and increasing insulin production in said patient in accord with said timed response.

45. The method as described in claim 44, comprising implanting a device in said patient which comprises receive means for receiving an externally generated food intake signal; algorithm means for storing and processing said algorithm; and insulin means for increasing insulin production in said patient.

46. The method as described in claim 45, comprising sensing at a predetermined patient location when said patient has had food intake.

47. A method of enhancing insulin production in a patient concurrently with the administration of a hypoglycemic agent to the patient, comprising determining when a said agent has been administered to the patient, and initiating a stimulation program following said determining, and stimulating insulin-producing islets in said patient in accord with said program.

48. A system for enhancing production of insulin by a patient's pancreas, comprising:

a stimulus generator for generating stimulus signals;

delivery means for delivering said stimulus signals to the patient's pancreas, having at least three electrodes positioned in or on said pancreas;

switching means for switching said signals to respective different pairs of said electrodes; and control means for controlling said stimulus generator to generate said stimulus pulses at a rate so as to increase pancreatic insulin production.

49. The system as described in claim 48, wherein said switching means comprises means for automatically switching said signals to a different pair of said electrodes in accordance with a predetermined program.

50. A system for delivering a timed insulin response to start of food intake by a patient, comprising:

intake means for determining when a patient has commenced and/or completed food intake;

algorithm means initiated by said intake means for determining a timed insulin production response following a said food intake; and insulin means for altering insulin production in said patient according to said timed insulin response.

51. The system as described in claim 50, comprising an implantable device housing said intake means and said insulin means, said implantable device further comprising receiver means for receiving an externally generated intake signal.

52. The system as described in claim 50, wherein said insulin means comprises stimulus means for stimulating the patient's pancreas with pulses timed to increase pancreatic insulin production.

53. The system as described in claim 50, wherein said patient has a transplant of islets of Langerhans, and said insulin means comprises stimulus means for stimulating said transplant with pulses timed to increase insulin production by said islets.

54. The system as described in claim 50, comprising glucose monitoring means for obtaining a measure of blood glucose, and further comprising adjust means for adjustably controlling said insulin means to produce insulin at a rate which is a function of said glucose measure.

55. The system as described in claim 54, wherein said adjust means comprises means for controlling said insulin means to decrease insulin production in response to an obtained glucose measure which is below a predetermined reference which represents hypoglycemia.

56. The system as described in claim 50, wherein said algorithm means comprises compensation means for introducing a compensated insulin response which is based upon insulin and glucose dynamics.

* * * * *